(12) United States Patent
Tanaka et al.

(10) Patent No.: US 11,166,921 B2
(45) Date of Patent: Nov. 9, 2021

(54) PATCH

(71) Applicant: HISAMITSU PHARMACEUTICAL CO., INC., Tosu (JP)

(72) Inventors: Yusuke Tanaka, Tosu (JP); Masahiro Sato, Tosu (JP); Kentaro Nakashima, Tosu (JP); Takaaki Yoshinaga, Tosu (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 0 days.

(21) Appl. No.: 16/963,537

(22) PCT Filed: Jan. 23, 2019

(86) PCT No.: PCT/JP2019/001981
§ 371 (c)(1),
(2) Date: Jul. 21, 2020

(87) PCT Pub. No.: WO2019/146614
PCT Pub. Date: Aug. 1, 2019

(65) Prior Publication Data
US 2020/0352872 A1 Nov. 12, 2020

(30) Foreign Application Priority Data
Jan. 24, 2018 (JP) .............................. JP2018-009835

(51) Int. Cl.
| *A61K 9/70* | (2006.01) |
| *A61K 31/045* | (2006.01) |
| *A61K 31/05* | (2006.01) |
| *A61K 31/125* | (2006.01) |
| *A61K 31/618* | (2006.01) |
| *A61K 36/534* | (2006.01) |

(52) U.S. Cl.
CPC .......... *A61K 9/7053* (2013.01); *A61K 31/045* (2013.01); *A61K 31/05* (2013.01); *A61K 31/125* (2013.01); *A61K 31/618* (2013.01); *A61K 36/534* (2013.01)

(58) Field of Classification Search
CPC .............. A61K 9/7053; A61K 2300/00; A61K 31/125; A61K 36/534; A61K 9/7076; A61K 31/045; A61K 31/05; A61K 31/618; A61K 31/165; A61K 47/32; A61K 9/70; A61K 47/06; A61K 47/44; A61K 9/7061; A61K 31/196; A61K 31/245; A61K 31/415; A61K 31/42; A61K 31/60; A61K 36/61; A61K 36/81; A61K 47/10; A61K 9/0014; A61K 9/7023; A61K 2039/54; A61K 2039/55511; A61K 31/35; A61K 39/0008; A61K 39/39; A61K 47/28; A61K 9/0021; A61K 9/08; A61K 9/7007; A61K 9/7069; A61K 31/075; A61K 31/08; A61K 31/137; A61K 31/138; A61K 31/216; A61K 31/343; A61K 31/407; A61K 31/465; A61K 31/517; A61K 33/08; A61K 45/06; A61K 47/02; A61K 47/18; A61K 47/34; A61K 8/34; A61K 8/345; A61K 9/06; A61K 9/703; A61K 9/7038; A61K 9/7084; A61P 29/00; A61P 17/00; A61P 43/00; A61P 25/04; A61P 23/00; A61P 37/04; A61P 11/14; A61P 13/10; A61P 25/00; A61P 25/08; A61P 25/28; A61P 29/02; A61Q 19/00
See application file for complete search history.

(56) References Cited

U.S. PATENT DOCUMENTS

| 2006/0093656 A1 | 5/2006 | Muta et al. |
| 2014/0171509 A1 | 6/2014 | Mori et al. |
| 2016/0271075 A1 | 9/2016 | Naruse et al. |
| 2017/0348246 A1 | 12/2017 | Tohara et al. |

FOREIGN PATENT DOCUMENTS

| CN | 106806893 A | 6/2017 |
| JP | 10-298065 A | 11/1998 |
| JP | 2003-183156 A | 7/2003 |
| JP | 2007-269753 A | 10/2007 |
| JP | 2008-179564 A | 8/2008 |
| JP | 2014-076960 A | 5/2014 |
| JP | 2014-177428 A | 9/2014 |

(Continued)

OTHER PUBLICATIONS

WO2017/170935 translation (Year: 2017).*
WO2017/146096 translation (Year: 2017).*
International Search Report for PCT/JP2019/001981 dated Mar. 26, 2019 [PCT/ISA/210].
International Preliminary Report on Patentability dated Jul. 28, 2020 with Written Opinion from the International Bureau in International Application No. PCT/JP2019/001981.

(Continued)

*Primary Examiner* — Audrea B Coniglio
*Assistant Examiner* — Audrea Buckley
(74) *Attorney, Agent, or Firm* — Sughrue Mion, PLLC

(57) ABSTRACT

The present invention provides a patch comprising a backing layer and an adhesive agent layer, wherein the adhesive agent layer is non-aqueous, the adhesive agent layer contains nonylic acid vanillylamide, terpene-based resin, rosin-based resin, styrene-isoprene-styrene block copolymer, and liquid paraffin, a mass ratio of a content of the terpene-based resin to a content of the rosin-based resin ((content of the terpene-based resin)/(content of the rosin-based resin)) in the adhesive agent layer is 0.45 to 1.3, and a mass ratio of a content of the styrene-isoprene-styrene block copolymer to a content of the liquid paraffin ((content of the styrene-isoprene-styrene block copolymer)/(content of the liquid paraffin)) in the adhesive agent layer is 0.45 to 1.2.

7 Claims, No Drawings

(56) References Cited

FOREIGN PATENT DOCUMENTS

| JP | 2018-168125 A | 11/2018 | | |
|----|---------------|---------|---|---|
| WO | 2004/047820 A1 | 6/2004 | | |
| WO | 2016/103999 A1 | 6/2016 | | |
| WO | 2017/146096 A1 | 8/2017 | | |
| WO | WO2017/146096 | * 8/2017 | ........... | A61K 31/165 |
| WO | 2017/170935 A1 | 10/2017 | | |
| WO | WO2017/170935 | * 10/2017 | ........... | A61K 31/167 |

OTHER PUBLICATIONS

Communication dated May 18, 2021 by the Singapore Patent Office in Singapore Application No. 11202007131U.
Extended European Search Report dated Sep. 24, 2021 in European Application No. 19743283.4.

* cited by examiner

PATCH

CROSS REFERENCE TO RELATED APPLICATIONS

This application is a National Stage of International Application No. PCT/JP2019/001981 filed Jan. 23, 2019, claiming priority based on Japanese Patent Application No. 2018-009835 filed Jan. 24, 2018.

TECHNICAL FIELD

The present invention relates to a patch, and more particularly to a patch containing nonylic acid vanillylamide.

BACKGROUND ART

As a preparation for the purpose of alleviating the symptoms of chronic diseases such as low back pain and stiff neck and upper back, warming sensation type external preparations for topically giving a warming sensation stimulus have been developed. It is considered that the warming sensation type external preparations exert an anti-inflammatory/analgesic effect on the chronic diseases by topically generating a thermal sensation using warming sensation stimulus ingredients, expanding the capillaries to promote blood circulation, and enhancing tissue metabolism.

Known examples of the warming sensation stimulus ingredients include capsicum extract, nonylic acid vanillylamide of synthetic capsicum, nicotinic acid ester, and the like. For example, Japanese Unexamined Patent Application Publication No. Hei 10-298065 (PTL 1) describes a patch in which a hydrophilic base layer containing water at 30 to 80% by weight is blended with at least one blood flow enhancer selected from vitamin E acetate, sodium polyethylene sulfonate, nonylic.acid vanillylamide, capsicum extract, capsicum powder, capsicum tincture, capsaicin, benzyl nicotinate, and pelargonic acid. In addition, for example, International Publication No. WO2004/047820 (PTL 2) discloses a warming sensation poultice containing a warming sensation imparting substance, 1-menthol, and polyethylene glycol, and describes, as the warming sensation imparting substance, capsaicin, dihydroxy capsaicin, capsanthin, capsaicinoid, capsicoside, capsicum extract, capsicum tincture, capsicum powder, benzyl nicotinate, nicotinic acid β-butoxyethyl, N-acyl vanillylamide, nonylic acid vanillylamide, vanillyl alcohol alkyl ether, and the like.

CITATION LIST

Patent Literature

[PTL 1] Japanese Unexamined Patent Application Publication No. Hei 10-298065
[PTL 2] International Publication No. WO2004/047820

SUMMARY OF INVENTION

Technical Problem

In order to continuously give a warming sensation stimulus to the application site, it is necessary to increase the thickness of the adhesive agent layer of the patch (preferably 250 μm or more). As a result of further studies on a patch containing nonylic acid vanillylamide as a warming sensation stimulus ingredient, particularly on a non-aqueous patch, the present inventors have found that, if the thickness of the adhesive agent layer in such a patch is increased, the cohesive force of the adhesive agent layer may be decreased, so that the adhesive agent layer may remain on the skin when the patch is removed, or that the tackiness of the adhesive agent layer may be decreased.

The present invention has been made in view of the above problems, and an object thereof is to provide a non-aqueous patch the adhesive agent layer of which has excellent cohesive force and tackiness.

Solution to Problem

The present inventors have made earnest studies to achieve the above object, and have found the following as a result. Even when the thickness of the adhesive agent layer is increased, a patch comprising a backing layer and an adhesive agent layer is capable of achieving a good cohesive force and tackiness of the adhesive agent layer if the adhesive agent layer is substantially water-free, non-aqueous, the adhesive agent layer contains a combination of nonylic acid vanillylamide, terpene-based resin, rosin-based resin, styrene-isoprene-styrene block copolymer, and liquid paraffin, and the mass ratio of the content of the terpene-based resin to the content of the rosin-based resin and the mass ratio of the content of the styrene-isoprene-styrene block copolymer to the content of the liquid paraffin are each in a specific range. Thus, the present invention has been completed.

A patch of the present invention is a patch comprising a backing layer and an adhesive agent layer, wherein the adhesive agent layer is non-aqueous, the adhesive agent layer contains nonylic acid vanillylamide, terpene-based resin, rosin-based resin, styrene-isoprene-styrene block copolymer, and liquid paraffin, a mass ratio of a content of the terpene-based resin to a content of the rosin-based resin ((content of the terpene-based resin)/(content of the rosin-based resin)) in the adhesive agent layer is 0.45 to 1.3, and a mass ratio of a content of the styrene-isoprene-styrene block copolymer to a content of the liquid paraffin ((content of the styrene-isoprene-styrene block copolymer)/(content of the liquid paraffin)) in the adhesive agent layer is 0.45 to 1.2.

In the patch of the present invention, preferably, a content of nonylic acid vanillylamide in the adhesive agent layer is 0.005 to 0.1% by mass based on a total mass of the adhesive agent layer. In addition, preferably, the adhesive agent layer is substantially water-free. Moreover, also preferably, the adhesive agent layer contains at least one anti-inflammatory analgesic agent selected from the group consisting of methyl salicylate, glycol salicylate, 1-menthol, dl-camphor, peppermint oil, and thymol. More preferably, a content of the anti-inflammatory analgesic agent in the adhesive agent layer is 1 to 10% by mass based on the total mass of the adhesive agent layer.

In addition, in the patch of the present invention, preferably, a thickness of the adhesive agent layer is 250 to 400 μm. Moreover, also preferably, a viscosity of the adhesive agent layer measured at 115° C. with a type B viscometer is 100 to 2500 dPa·s.

Advantageous Effects of Invention

The present invention makes it possible to provide a non-aqueous patch the adhesive agent layer of which has excellent cohesive force and tackiness.

DESCRIPTION OF EMBODIMENTS

Hereinafter, the present invention is described in detail with reference to its preferred embodiments. A patch of the present invention is a patch comprising a backing layer and an adhesive agent layer, wherein the adhesive agent layer is non-aqueous, the adhesive agent layer contains nonylic acid vanillylamide, terpene-based resin, rosin-based resin, styrene-isoprene-styrene block copolymer, and liquid paraffin, a mass ratio of a content of the terpene-based resin and a content of the rosin-based resin ((content of the terpene-based resin)/(content of the rosin-based resin)) in the adhesive agent layer is 0.45 to 1.3, and a mass ratio of a content of the styrene-isoprene-styrene block copolymer and a content of the liquid paraffin ((content of the styrene-isoprene-styrene block copolymer)/(content of the liquid paraffin)) in the adhesive agent layer is 0.45 to 1.2.

The patch of the present invention includes a backing layer and an adhesive agent layer. The backing layer is not particularly limited as long as it can back the adhesive agent layer to be described later, and any known backing layer for patches can be appropriately used. Material for the backing layer according to the present invention are illustrated by synthetic resins which include polyolefins such as polyethylene and polypropylene; ethylene-vinyl acetate copolymers, vinyl acetate-vinyl chloride copolymers, polyvinyl chloride, and the like; polyamides such as nylon; polyesters such as polyethylene terephthalate (PET), polybutylene terephthalate, and polyethylene naphthalate; cellulose derivatives; and polyurethane, as well as metals which include aluminum. Among these, polyesters and polyethylene terephthalate are preferable from the viewpoints of drug non-adsorption property and drug impermeable property. Examples of the form of the backing layer include films; sheet-shaped articles such as sheets, sheet-shaped porous bodies, and sheet-shaped foamed bodies; fabrics such as woven fabrics, knitted fabrics, and non-woven fabrics; foils; and laminates thereof. In addition, the thickness of the backing layer is not particularly limited, but is preferably in the range of 5 to 1000 μm from the viewpoints of workability when applying the patch and ease of production.

The patch of the present invention may further include a release liner on the surface of the adhesive agent layer opposite to the backing layer. The release liner is illustrated by a film, a sheet, and a laminate thereof, which are made of materials such as synthetic resins which include polyolefins such as polyethylene and polypropylene; ethylene-vinyl acetate copolymers, vinyl acetate-vinyl chloride copolymers, polyvinyl chloride, and the like; polyamides such as nylon; polyesters such as polyethylene terephthalate; cellulose derivatives; and polyurethane, as well as other materials such as aluminum and paper. Preferably, these release liners are subjected to a release treatment such as a silicone-containing compound coat or a fluorine-containing compound coat on the surface in contact with the adhesive agent layer so that they can be easily released from the adhesive agent layer.

The patch of the present invention is a non-aqueous patch, and the adhesive agent layer according to the present invention needs to be a non-aqueous adhesive agent layer. In the present invention, the "non-aqueous adhesive agent layer" means that the adhesive agent layer is substantially water-free, and examples of the water include purified water, sterilized water, natural water, and a mixture thereof. In the present invention, the phrase "substantially water-free" means that there is no step of intentionally blending water into the adhesive agent layer during the production step, and does not exclude moisture in the air or the like contained during the production step or moisture having absorbed sweat or the like during application of the patch to the skin. More specifically, the content of water in such an adhesive agent layer is preferably less than 1% by mass, more preferably 0.99% by mass or less, and further preferably 0 to 0.5% by mass based on the total mass of the adhesive agent layer.

The adhesive agent layer according to the present invention contains nonylic acid vanillylamide (also referred to as "nonylic acid vanillamide") as a warming sensation stimulus ingredient. In the present invention, the content of nonylic acid vanillylamide contained in the adhesive agent layer is preferably 0.005 to 0.1% by mass, more preferably 0.01 to 0.02% by mass, further preferably 0.01 to 0.018% by mass, and still more preferably 0.012 to 0.016% by mass based on the total mass of the adhesive agent layer. When the content of nonylic acid vanillylamide is less than the lower limit, the warming sensation stimulus given to the application site is insufficient and the thermal sensation tends to be lowered. Meanwhile, when the content of nonylic acid vanillylamide is more than the upper limit, the warming sensation stimulus given to the application site tends to be too strong, the cohesive force of the adhesive agent layer tends to be decreased, and an unpleasant odor tends to occur.

The adhesive agent layer according to the present invention contains terpene-based resin. In the present invention, the terpene-based resin is a resin having isoprene as a constituent unit, and examples of the terpene-based resin according to the present invention include pinene polymers (such as α-pinene polymer and β-pinene polymer), terpene polymers, dipentene polymers, terpene-phenol polymers, aromatic modified terpene polymers, and pinene-phenol copolymers, and one of these may be used alone, or two or more thereof may be used in combination. As the terpene-based resin, commercially available products such as YS RESIN (such as YS RESIN PXN, YS RESIN PX1150N, YS RESIN PX1000, YS RESIN TO125, and YS RESIN TO105), CLEARON P105, CLEARON M115, CLEARON K100 (these are trade names, manufactured by YASUHARA CHEMICAL CO., LTD.), and TAMANOL 901 (trade name, manufactured by Arakawa Chemical Industries, Ltd.) may be appropriately used, and one of these may be used alone, or two or more thereof may be used in combination. Among these, the terpene-based resin according to the present invention is more preferably a pinene polymer from the viewpoint that the tackiness of the adhesive agent layer and the adhesiveness to the skin tend to be better.

In the present invention, the content of the terpene-based resin contained in the adhesive agent layer (in the case of two or more kinds, the total content thereof, and the same applies hereinafter) is preferably 1 to 25% by mass, more preferably 4 to 22% by mass, and further preferably 5 to 11% by mass based on the total mass of the adhesive agent layer. When the content of the terpene-based resin is less than the lower limit, the tackiness of the adhesive agent layer and the adhesiveness to the skin tend to be decreased. Meanwhile, when the content of the terpene-based resin is more than the upper limit, the adhesive agent layer may remain on the skin when the patch is removed, or the pain at the time of releasing tends to increase.

The adhesive agent layer according to the present invention also contains rosin-based resin. In the present invention, the rosin-based resin is a resin whose main ingredient is rosin acid, and examples of the rosin-based resin according to the present invention include hydrogenated rosin glycerin ester, ultralight rosin, ultralight rosin ester, and acid-modified ultralight rosin, and one of these may be used alone, or two or more thereof may be used in combination. As the rosin-based resin, commercially available products such as PINECRYSTAL (such as KE-311, PE-590, KE-359, and KE-100) (trade name, manufactured by Arakawa Chemical Industries, Ltd.) may be appropriately used, and one of these may be used alone, or two or more thereof may be used in combination. Among these, the rosin-based resin according to the present invention is more preferably hydrogenated rosin glycerin ester from the viewpoint that the tackiness of the adhesive agent layer and the adhesiveness to the skin tend to be better.

In the present invention, the content of the rosin-based resin contained in the adhesive agent layer (in the case of two or more kinds, the total content thereof, and the same applies hereinafter) is preferably 1 to 25% by mass, more preferably 5 to 22% by mass, and further preferably 10 to 14% by mass based on the total mass of the adhesive agent layer. When the content of the rosin-based resin is less than the lower limit, the tackiness of the adhesive agent layer and the adhesiveness to the skin tend to be decreased, or the viscosity tends to be too high. Meanwhile, when the content of the rosin-based resin is more than the upper limit, the adhesive agent layer may remain on the skin when the patch is removed, or the pain at the time of releasing tends to increase.

In addition, in the present invention, the mass ratio of the content of the terpene-based resin and the content of the rosin-based resin ((content of the terpene-based resin)/(content of the rosin-based resin)) in the adhesive agent layer needs to be 0.45 to 1.3. In addition, the mass ratio is preferably 0.45 to 1.0, and more preferably 0.50 to 1.0. When the content of the terpene-based resin based on the content of the rosin-based resin is less than the lower limit, the tackiness of the adhesive agent layer and the adhesiveness to the skin tend to be decreased. Meanwhile, when the content of the terpene-based resin based on the content of the rosin-based resin is more than the upper limit, the adhesive agent layer tends to easily remain on the skin when the patch is removed.

The adhesive agent layer according to the present invention contains a styrene-isoprene-styrene block copolymer (SIS). In the present invention, the content of the styrene-isoprene-styrene block copolymer contained in the adhesive agent layer is preferably 15 to 34% by mass, more preferably 16 to 34% by mass, and further preferably 20 to 28% by mass based on the total mass of the adhesive agent layer. When the content of the styrene-isoprene-styrene block copolymer is less than the lower limit, the adhesive agent layer tends to easily remain on the skin when the patch is removed. Meanwhile, when the content of the styrene-isoprene-styrene block copolymer is more than the upper limit, the tackiness of the adhesive agent layer and the adhesiveness to the skin tend to be decreased, or the viscosity tends to be too high.

The adhesive agent layer according to the present invention also contains liquid paraffin. The liquid paraffin is a paraffinic process oil also called liquid paraffin, mineral oil, and white mineral oil. The liquid paraffin according to the present invention has a kinematic viscosity at 37.8° C. of preferably 5.8 to 100 mm$^2$/s, and more preferably 68 to 96 mm$^2$/s. When the kinematic viscosity is less than the lower limit, the adhesive agent layer tends to easily remain on the skin when the patch is removed, or the tackiness of the adhesive agent layer and the adhesiveness to the skin tend to be decreased. Meanwhile, when the kinematic viscosity is more than the upper limit, the viscosity of the adhesive agent layer tends to be too high.

In the present invention, the content of the liquid paraffin contained in the adhesive agent layer is preferably 20 to 45% by mass, more preferably 22 to 42% by mass, and further preferably 25 to 41% by mass based on the total mass of the adhesive agent layer. When the content of the liquid paraffin is less than the lower limit, the viscosity of the adhesive agent layer tends to be too high. Meanwhile, when the content of the liquid paraffin is more than the upper limit, the adhesive agent layer tends to easily remain on the skin when the patch is removed, or the tackiness of the adhesive agent layer and the adhesiveness to the skin tend to be decreased.

In addition, in the present invention, the mass ratio of the content of the styrene-isoprene-styrene block copolymer and the content of the liquid paraffin ((content of the styrene-isoprene-styrene block copolymer)/(content of the liquid paraffin)) in the adhesive agent layer needs to be 0.45 to 1.2. In addition, the mass ratio is preferably 0.45 to 1.0, and more preferably 0.5 to 1.0. When the content of the styrene-isoprene-styrene block copolymer based on the content of the liquid paraffin is less than the lower limit, the adhesive agent layer tends to easily remain on the skin when the patch is removed. Meanwhile, when the content of the styrene-isoprene-styrene block copolymer based on the content of the liquid paraffin is more than the upper limit, the tackiness the adhesive agent layer and the adhesiveness to the skin tend to be decreased.

Preferably, the adhesive agent layer according to the present invention further contains at least one anti-inflammatory analgesic agent selected from the group consisting of methyl salicylate, glycol salicylate, l-menthol, dl-camphor, peppermint oil, and thymol. By using these anti-inflammatory analgesic agents in combination with nonylic acid vanillylamide, it is possible to make better the warming sensation stimulus derived from nonylic acid vanillylamide. Among these, the anti-inflammatory analgesic agent is preferably at least one selected from the group consisting of methyl salicylate, glycol salicylate, and l-menthol, and more preferably a combination of glycol salicylate and l-menthol, from the viewpoints of an appropriate anti-inflammatory analgesic effect and a tendency to give an appropriate stimulating sensation to the application site.

In the present invention, when the adhesive agent layer contains the anti-inflammatory analgesic agent, the content of the anti-inflammatory analgesic agent contained in the adhesive agent layer (in the case of two or more kinds, the total content thereof, and the same applies hereinafter) is preferably 1 to 10% by mass, more preferably 1.5 to 9% by mass, and further preferably 2.55 to 7.66% by mass based on the total mass of the adhesive agent layer. When the content of the anti-inflammatory analgesic agent is less than the lower limit, the anti-inflammatory analgesic effect tends to be insufficient. Meanwhile, when the content of the anti-inflammatory analgesic agent is more than the upper limit, it tends to be difficult to uniformly contain it in the adhesive agent layer.

The adhesive base of the adhesive agent layer according to the present invention may further contain an additional adhesive base other than the styrene-isoprene-styrene block copolymer. Such an adhesive base is not particularly limited as long as it is substantially water-free, and examples thereof include an additional rubber-based adhesive base other than styrene-isoprene-styrene block copolymer, an acrylic adhesive base, and a silicone adhesive base.

Examples of the additional rubber-based adhesive base include polyisobutylene (PIB), isoprene, styrene-butadiene-styrene block copolymers (SBS), styrene-butadiene rubber (SBR), polybutene, and natural rubber, and one of these may be used alone, or two or more thereof may be used in combination. Among these, the rubber-based adhesive base used is preferably polyisobutylene from the viewpoint that the tackiness of the adhesive agent layer and the adhesiveness to the skin tend to be better in the combination with the styrene-isoprene-styrene block copolymer. When the styrene-isoprene-styrene block copolymer and polyisobutylene are used in combination, the mass ratio of the styrene-isoprene-styrene block copolymer and the polyisobutylene ((mass of the styrene-isoprene-styrene block copolymer):(mass of the polyisobutylene)) is, for example, more preferably 1:0.28 to 1:0.58 (further preferably in the range of 1:0.33 to 1:0.44).

Examples of the acrylic adhesive base include acrylic acid/acrylic acid octyl ester copolymer, 2-ethylhexyl acrylate/vinylpyrrolidone copolymer, acrylic ester/vinyl acetate copolymer, 2-ethylhexyl acrylate/2-ethylhexylmethacrylate/dodecyl methacrylate copolymer, methyl acrylate/2-ethylhexyl acrylate copolymer resin, 2-ethylhexyl acrylate/methyl acrylate/acrylic acid/glycidyl methacrylate copolymer, 2-ethylhexyl acrylate/vinyl acetate/hydroxyethyl acrylate/glycidyl methacrylate copolymer, 2-ethylhexyl acrylate/diacetone acrylamide/acetoacetoxyethyl methacrylate/methyl methacrylate copolymer, ethyl acrylate/methyl methacrylate copolymer, and acrylic polymer contained in an acrylic resin alkanolamine liquid, which are listed in "IyakuhinTenkabutuJiten 2016 (edited by Nippon Iyakuhin Tenka Zai Kyokai)" as adhesive agents, and one of these may be used alone, or two or more thereof may be used in combination.

Examples of the silicone-based adhesive base include polydimethyl siloxane (such as a polymer represented by MQ in ASTM D-1418), polymethyl vinyl siloxane (such as a polymer represented by VMQ in ASTM D-1418), and polymethyl phenyl siloxane (such as a polymer represented by PVMQ in ASTM D-1418), and one of these may be used alone, or two or more thereof may be used in combination.

In the present invention, when the adhesive agent layer contains these additional adhesive bases, the content of the additional adhesive bases contained in the adhesive agent layer (in the case of two or more kinds, the total content thereof, and the same applies hereinafter) is preferably 50% by mass or less, and more preferably 5 to 44% by mass based on the total mass of the adhesive agent layer.

The adhesive agent layer according to the present invention may further contain an absorption enhancer (transdermal absorption enhancer) having an action of promoting transdermal absorption of active ingredients. Examples of the absorption enhancer include aliphatic alcohols, fatty acids having 6 to 20 carbon atoms, fatty acid esters, fatty acid amides, or aliphatic alcohol ethers; aromatic organic acids; aromatic alcohols; aromatic organic acid esters or ethers; POE hydrogenated castor oils; lecithins; phospholipids; soybean oil derivatives; and triacetin, and one of these may be used alone, or two or more thereof may be used in combination.

In the present invention, when the adhesive agent layer contains the absorption enhancer, the content of the absorption enhancer contained in the adhesive agent layer (in the case of two or more kinds, the total content thereof, and the same applies hereinafter) is preferably 15% by mass or less, more preferably 12% by mass or less, and further preferably 10% by mass or less based on the total mass of the adhesive agent layer.

In addition, the adhesive agent layer according to the present invention may further contain an additional active ingredient other than nonylic acid vanillylamide and the anti-inflammatory analgesic agent described above, an additional tackifier other than the terpene-based resin and the rosin-based resin, an antioxidant, a plasticizer, a filler, a solubilizer, and the like in an appropriate amount if necessary, as long as the effects of the present invention are not impaired.

Examples of the additional active ingredient other than nonylic acid vanillylamide and the anti-inflammatory analgesic agent described above include plant-derived ingredients such as Amur cork tree powder and glycyrrhetinic acid; and medicinal ingredients such as non-steroidal anti-inflammatory analgesic agents (such as diclofenac, indomethacin, ketoprofen, felbinac, loxoprofen, ibuprofen, flurbiprofen, tiaprofen, acemetacin, sulindac, etodolac, tolmetin, piroxicam, meloxicam, ampiroxicam, naproxen, azapropazone, valdecoxib, celecoxib, rofecoxib, and amfenac), antipyretic analgesic drugs (such as acetaminophen), antihistaminic agents (such as diphenhydramine, chlorpheniramine, mequitazine, and homochlorcyclizine), antihypertensive agents (such as diltiazem, nicardipine, nilvadipine, metoprolol, bisoprolol, and trandolapril), Anti-Parkinsonian agents (such as pergolide, ropinirole, bromocriptine, and selegiline), bronchodilating agents (such as tulobuterol, isoproterenol, and salbutamol), antiallergic agents (such as ketotifen, loratadine, azelastine, terfenadine, cetirizine, and acitazanolast), topical anesthetic agents (such as lidocaine and dibucaine), neuropathic pain treatment drugs (such as pregabalin), non-narcotic analgesic drugs (buprenorphine, tramadol, and pentazocine), anesthesia-based analgesic agents (such as morphine, oxycodone, and fentanyl), urinary organ affecting agents (such as oxybutynin and tamsulosin), brain-nerve affecting agents (such as promazine and chlorpromazine), steroid hormone agents (such as estradiol, progesterone, norethisterone, cortisone, and hydrocortisone), antidepressant agents (such as sertraline, fluoxetine, paroxetine, and citalopram), anti-dementia drugs (such as donepezil, rivastigmine, and galantamine), antipsychotic drugs (such as risperidone and olanzapine), central nervous system stimulating agents (such as methylphenidate), osteoporosis treatment drugs (such as raloxifene and alendronate), breast cancer preventive drugs (such as tamoxifen), anti-obesity drugs (such as mazindol and sibutramine), insomnia-improving drugs (such as melatonin), and anti-rheumatic drugs (such as actarit), and one of these may be used alone, or two or more thereof may be used in combination.

In the present invention, when the adhesive agent layer contains the additional active ingredient, the content of the additional active ingredient contained in the adhesive agent layer (in the case of two or more kinds, the total content thereof, and the same applies hereinafter) is preferably 5% by mass or less, more preferably 0.5 to 5% by mass, further preferably 0.5 to 4% by mass, and still more preferably 1 to 3% by mass based on the total mass of the adhesive agent layer, although it cannot be said unconditionally because the content is adjusted appropriately depending on the purpose of treatment.

Examples of the additional tackifier other than the terpene-based resin and the rosin-based resin include petroleum-based resin (such as alicyclic saturated hydrocarbon resin which is a homopolymer or copolymer of an alicyclic hydrocarbon monomer), phenol-based resin, and xylene-based resin, and one of these may be used alone, or two or more thereof may be used in combination. In the present invention, when the adhesive agent layer contains the additional tackifier, the content of the tackifier contained in the adhesive agent layer (in the case of two or more kinds, the total content thereof, and the same applies hereinafter) is preferably 30% by mass or less, and more preferably 25% by mass or less based on the total mass of the adhesive agent layer.

Examples of the antioxidant include ascorbic acid, propyl gallate, butylhydroxyanisole, dibutylhydroxytoluene, nordihydroguaiaretic acid, tocopherol, tocopherol acetate, and sodium hydrogen sulfite, and one of these may be used alone, or two or more thereof may be used in combination. In the present invention, when the adhesive agent layer contains the antioxidant, the content of the antioxidant contained in the adhesive agent layer (in the case of two or more kinds, the total content thereof, and the same applies hereinafter) is, for example, preferably 5% by mass or less, more preferably 0.1 to 5% by mass, further preferably 3% by mass or less, and still more preferably 0.1 to 1% by mass based on the total mass of the adhesive agent layer.

Examples of the plasticizer include silicone oils; petroleum-based oils such as additional paraffinic process oils (other than the liquid paraffin), naphthenic process oils, and aromatic process oils; squalane and squalene; vegetable-based oils such as olive oil, camellia oil, castor oil, tall oil, and peanut oil; dibasic acid esters such as dibutyl phthalate and dioctyl phthalate; liquid rubbers such as polybutene and liquid isoprene rubber; and diethylene glycol, polyethylene glycol, propylene glycol, and dipropylene glycol, and one of these may be used alone, or two or more thereof may be used in combination. In the present invention, when the adhesive agent layer contains the plasticizer, the content of the plasticizer contained in the adhesive agent layer (in the case of two or more kinds, the total content thereof, and the same applies hereinafter) is, for example, preferably 50% by mass or less, and more preferably 40% by mass or less based on the total mass of the adhesive agent layer.

Examples of the filler include carbonates such as calcium carbonate and magnesium carbonate; silicates such as magnesium silicate; silicic acid, aluminum silicate, aluminum hydroxide, barium sulfate, calcium sulfate, calcium zincate, zinc oxide, and titanium oxide, and one of these may be used alone, or two or more thereof may be used in combination. Among these, preferably, the filler is at least one selected from the group consisting of titanium oxide, aluminum hydroxide, and aluminum silicate. In the present invention, when the adhesive agent layer contains the filler, the content of the filler contained in the adhesive agent layer (in the case of two or more kinds, the total content thereof, and the same applies hereinafter) is, for example, preferably 7% by mass or less, more preferably 0.5 to 7% by mass, further preferably 0.5 to 5.5% by mass, and still more preferably 1 to 5% by mass based on the total mass of the adhesive agent layer.

Examples of the solubilizer include benzyl alcohol; pirotiodecane; isopropyl myristate; crotamiton; pyrrolidones such as N-methyl-2-pyrrolidone; higher alcohols; and polybasic acid esters such as diethyl adipate, isopropyl adipate, diisopropyl adipate, diisobutyl adipate, dioctyl adipate, di(2-heptylundecyl)adipate, diisopropyl sebacate, and diethyl sebacate, and one of these may be used alone, or two or more thereof may be used in combination. In the present invention, when the adhesive agent layer contains the solubilizer, the content of the solubilizer contained in the adhesive agent layer (in the case of two or more kinds, the total content thereof, and the same applies hereinafter) is, for example, preferably 10% by mass or less based an the total mass of the adhesive agent layer.

In such an adhesive agent layer according to the present invention. The viscosity measured at 115° C. with a type B viscometer (Brookfield rotational viscometer) is preferably 100 to 2500 dPa·s, more preferably 500 to 2500 dPa·s, further preferably 1000 to 2500 dPa·s, and still more preferably 1100 to 2500 dPa·s. When the viscosity is within such a range, it is possible to achieve better production suitability such as the coating of the adhesive agent layer, and it is possible to achieve a better cohesive force and tackiness of the adhesive agent layer.

The thickness of the adhesive agent layer according to the present invention is not particularly limited, but is preferably 80 to 400 µm, and more preferably 110 to 380 µm. The adhesive agent layer according to the present invention exhibits excellent cohesive force and tackiness of the adhesive agent layer even when the thickness of the adhesive agent layer is increased. For this reason, the thickness of the adhesive agent layer may be 250 to 400 µm, and more preferably 280 to 360 µm, for example.

In addition, the area of the application surface of the adhesive agent layer according to the present invention can be appropriately adjusted according to the purpose of treatment and the target of application, and is not particularly limited, but is usually in the range of 0.5 to 200 cm$^2$. Moreover, the shape of the application surface of the adhesive agent layer according to the present invention is not particularly limited, and it is possible to employ any shape such as a round shape, an elliptical shape, a square shape, and a rectangular shape.

The patch of the present invention is not particularly limited, and can be produced by appropriately employing a known method for producing a non-aqueous patch. For example, first, nonylic acid vanillylamide, terpene-based resin, rosin-based resin, styrene-isoprene-styrene block copolymer, liquid paraffin, and, if necessary, the above-described additional ingredients are mixed in a usual manner to obtain a uniform adhesive agent layer composition. Next, this adhesive agent layer composition is applied on the surface (usually on one surface) of the backing layer to the desired mass per unit area, which is then cut into a desired shape if necessary. Thereby, the patch of the present invention can be obtained.

In addition, the method for producing the patch of the present invention may further include a step of attaching the release liner on the surface of the adhesive agent layer opposite to the backing layer. Further, the method for producing the patch of the present invention may include steps of first applying the adhesive agent layer composition on one surface of the release liner to the desired mass per unit area to form an adhesive agent layer, then attaching the backing layer on the surface of the adhesive agent layer opposite to the release liner, and cutting it into a desired shape if necessary, to thereby obtain the patch of the present invention. Moreover, the obtained patch may be, if necessary, enclosed in a packaging container for storage (for example, an aluminum laminated bag) to form a package.

EXAMPLES

Hereinafter, the present invention is described more specifically based on Examples and Comparative Examples, but the present invention is not limited to the following Examples. Note that, in each of the Examples and Comparative Examples, the tackiness and residual adhesive agent layer evaluation tests as well as adhesive agent layer viscosity measurement were performed by the methods described below.

Tackiness and Residual Adhesive Agent Layer Evaluation Tests

Each of the patches was cut into circles having a diameter of 25 mm to release the release liners. Each of 6 or 7 subjects touched the surface (adhesive surface) of each adhesive agent layer with a finger, and evaluated the tackiness of each adhesive agent layer to the skin according to the following tackiness evaluation criteria:

Tackiness Evaluation

0: The tackiness is extremely low
25: The tackiness is low
50: The tackiness is somewhat low
75: The tackiness is somewhat high
100: The tackiness is extremely high.

In addition, the subjects evaluated the residual adhesive agent layer (paste) on the finger surfaces at the time of tackiness evaluation according to the following criteria for residual adhesive agent layer evaluation:

Residual Adhesive Agent Layer Evaluation

0: The adhesive agent layer remained on the finger surfaces to the extent that it was annoying (remained on the entire finger surfaces)
25: The adhesive agent layer remained on part of the finger surfaces
50: There was a small amount of the adhesive agent layer remaining on the finger surfaces, but a large extent of sticky strings was observed when the fingers were released from the surface of the adhesive agent layer
75: A slight extent of sticky strings was observed when the fingers were released from the surface of the adhesive agent layer
100: There was no adhesive agent layer remaining on the finger surfaces, and no sticky strings were observed.

Here, the "sticky strings" are a phenomenon that is more often observed as the cohesive force of the adhesive agent layer is smaller, and mean that part of the adhesive agent layer is released in the form of stretching strings, so that the adhesive agent layer is deformed.

Regarding the evaluation values for each of the tackiness evaluation and the residual adhesive agent layer evaluation obtained from the subjects, the sum of the obtained values was divided by the number of subjects to calculate the average value, which was used as a value for the evaluation. Note that, in the tackiness evaluation, a value of 75 to 100 is recognized as having an acceptable level because the tackiness of the adhesive agent layer to the skin is good, and in the residual adhesive agent layer evaluation, a value of 63 to 100 is recognized as having an acceptable level because the cohesive force of the adhesive agent layer is good.

Adhesive Agent Layer Viscosity Measurement

A certain amount of the adhesive agent layer was scraped off at room temperature from each of the patches obtained in Examples and Comparative Examples, which was heated to 115° C. While the temperature was maintained at 115° C., the rotor of a type B viscometer (apparatus: Viscotester VT-04F, manufacturer: RION CO., LTD.) was immersed and rotated. The viscous resistance (torque) acting on this rotor was measured and taken as the viscosity (dPa·s) of the adhesive agent layer at 115° C.

Example 1

First, 0.012 parts by mass of nonylic acid vanillylamide, 1.70 parts by mass of Amur cork tree powder, 2.55 parts by mass of glycol salicylate, 5.11 parts by mass of 1-menthol, 5.00 parts by mass of terpene-based resin (TP) (YS RESIN PX1150N, manufactured by YASUHARA CHEMICAL CO., LTD.), 10.00 parts by mass of rosin-based resin (RS) (PINECRYSTAL KE-311, manufactured by Arakawa Chemical Industries, Ltd.), 21.79 parts by mass of styrene-isoprene-styrene block copolymer (SIS), 9.40 parts by mass of polyisobutylene, 40.828 parts by mass of liquid paraffin (LP), and 3.61 parts by mass of additional ingredients (antioxidant and filler) were mixed to obtain an adhesive agent layer composition. Then, the obtained adhesive agent layer composition was applied onto a release liner (a polyethylene terephthalate film subjected to a release treatment) to form an adhesive agent layer such that the adhesive agent layer had a thickness of 320 μm. A backing layer (polyester nonwoven fabric) was laminated on the surface of the obtained adhesive agent layer opposite to the release liner to obtain a patch in which backing layer/adhesive agent layer/release liner were laminated in this order.

Examples 2 to 5 and Comparative Examples 1 to 6

Each of the patches was obtained in the same manner as in Example 1 except that the compositions of the adhesive agent layer compositions were changed to the compositions presented in Tables 1 and 2 below.

Comparative Examples 7 and 8

Each of the patches was obtained in the same manner as in Example 1 except that the compositions of the adhesive agent layer compositions were changed to the compositions presented in Table 3 below and the thickness of the adhesive agent layer was 260 μm (Comparative Example 7) or 400 μm (Comparative Example 8).

The patches obtained in Examples 1 to 5 and Comparative Examples 1 to 8 were subjected to tackiness evaluation and residual adhesive agent layer evaluation tests as well as adhesive agent layer viscosity measurement. The results are presented in Tables 1 to 3 below together with the compositions of the adhesive agent layer compositions of Examples and Comparative Examples. In addition, Tables 1 to 3 also present the mass ratio of the content of terpene-based resin and the content of rosin-based resin (TP/RS), and the mass ratio of the content of styrene-isoprene-styrene block copolymer and the content of liquid paraffin (SIS/LP) in the adhesive agent layer. Note that, the tables below, "N.D." in viscosity indicates that the measurement limit of viscosity measurement (4000 dPa·s) was exceeded.

TABLE 1

| | Comp. Ex. 1 | Comp. Ex. 2 | Ex. 1 | Ex. 2 | Ex. 3 | Ex. 4 | Comp. Ex. 3 | Comp. Ex. 4 |
|---|---|---|---|---|---|---|---|---|
| Adhesive Agent Layer Composition [Parts by Mass] | | | | | | | | |
| Nonylic Acid Vanillylamide | 0.012 | 0.012 | 0.012 | 0.016 | 0.012 | 0.012 | 0.012 | 0.012 |
| Amur Cork Tree Powder | 1.70 | 1.70 | 1.70 | 1.70 | 1.70 | 1.70 | 1.70 | 1.70 |
| Glycol Salicylate | 2.55 | 2.55 | 2.55 | 2.55 | 2.55 | 2.55 | 2.55 | 2.55 |
| l-Menthol | 5.11 | 5.11 | 5.1 | 5.11 | 5.11 | 5.11 | 5.1 | 5.11 |
| Terpene-Based Resin (TP) | — | 4.00 | 5.00 | 8.00 | 10.00 | 11.00 | 10.00 | 22.00 |
| Rosin-Based Resin (RS) | 22.00 | 10.00 | 10.00 | 14.00 | 14.00 | 11.00 | 5.00 | — |
| Styrene-Isoprene-Styrene Block Copolymer (SIS) | 21.79 | 21.79 | 21.79 | 21.79 | 21.79 | 21.79 | 21.79 | 21.79 |
| Polyisobutylene | 9.40 | 9.40 | 9.40 | 9.40 | 9.40 | 9.40 | 9.40 | 9.40 |
| Liquid Paraffin (LP) | 33.828 | 41.828 | 40.828 | 33.824 | 31.828 | 33.828 | 40.828 | 33.828 |
| Additional Ingredients | 3.61 | 3.61 | 3.61 | 3.61 | 3.61 | 3.61 | 3.61 | 3.61 |
| Total | 100 | 100 | 100 | 100 | 100 | 100 | 100 | 100 |
| TP/RS | — | 0.40 | 0.50 | 0.57 | 0.71 | 1.00 | 2.00 | — |
| SIS/LP | 0.64 | 0.52 | 0.53 | 0.64 | 0.68 | 0.64 | 0.53 | 0.64 |
| Evaluation | | | | | | | | |
| Tackiness | 63 | 71 | 81 | 88 | 86 | 93 | 100 | 100 |
| Residual Adhesive Agent Layer | 100 | 96 | 81 | 88 | 79 | 68 | 44 | 25 |
| Viscosity [dPa · S] | 900 | 1000 | 1500 | 1200 | 1300 | 1500 | 900 | 1000 |

TABLE 2

| | Comp. Ex. 5 | Ex. 1 | Ex. 2 | Ex. 5 | Comp. Ex. 6 |
|---|---|---|---|---|---|
| Adhesive Agent Layer Composition [Parts by Mass] | | | | | |
| Nonylic Acid Vanillylamide | 0.012 | 0.012 | 0.016 | 0.012 | 0.012 |
| Amur Cork Tree Powder | 1.70 | 1.70 | 1.70 | 1.70 | 1.70 |
| Glycol Salicylate | 2.55 | 2.55 | 2.55 | 2.55 | 2.55 |
| l-Menthol | 5.11 | 5.11 | 5.11 | 5.11 | 5.11 |
| Terpene-Based Resin (TP) | 8.00 | 5.00 | 8.00 | 8.00 | 8.00 |
| Rosin-Based Resin (RS) | 14.00 | 10.00 | 14.00 | 14.00 | 14.00 |
| Styrene-Isoprene-Styrene Block Copolymer (SIS) | 16.00 | 21.79 | 21.79 | 27.81 | 33.37 |
| Polyisobutylene | 9.40 | 9.40 | 9.40 | 9.40 | 9.40 |
| Liquid Paraffin (LP) | 39.618 | 40.828 | 33.824 | 27.808 | 22.248 |
| Additional Ingredients | 3.61 | 3.61 | 3.61 | 3.61 | 3.61 |
| Total | 100 | 100 | 100 | 100 | 100 |
| TP/RS | 0.57 | 0.50 | 0.57 | 0.57 | 0.57 |
| SIS/LP | 0.40 | 0.53 | 0.64 | 1.00 | 1.50 |
| Evaluation | | | | | |
| Tackiness | 96 | 81 | 88 | 79 | 71 |
| Residual Adhesive Agent Layer | 58 | 81 | 88 | 96 | 100 |
| Viscosity [dPa · S] | 500 | 1500 | 1200 | 2000 | N.D. |

TABLE 3

|  | Comp. Ex. 7 | Ex. 1 | Comp. Ex. 8 |
|---|---|---|---|
| Adhesive Agent Layer Composition [Parts by Mass] | | | |
| Nonylic Acid Vanillylamide | 0.012 | 0.012 | 0.012 |
| Amur Cork Tree Powder | 1.70 | 1.70 | 1.70 |
| Glycol Salicylate | 2.55 | 2.55 | 2.55 |
| l-Menthol | 5.11 | 5.11 | 5.11 |
| Terpene-Based Resin (TP) | 18.00 | 5.00 | 18.00 |
| Rosin-Based Resin (RS) | — | 10.00 | — |
| Styrene-Isoprene-Styrene Block Copolymer (SIS) | 21.79 | 21.79 | 21.79 |
| Polyisobutylene | 9.40 | 9.40 | 9.40 |
| Liquid Paraffin (LP) | 37.828 | 40.828 | 37.828 |
| Additional Ingredients | 3.61 | 3.61 | 3.61 |
| Total | 100 | 100 | 100 |
| Thickness of Adhesive Agent Layer [μm] | 260 | 320 | 400 |
| SIS/LP | 0.58 | 0.53 | 0.58 |
| Evaluation | | | |
| Tackiness | 83 | 81 | 86 |
| Residual Adhesive Agent Layer | 61 | 81 | 36 |
| Viscosity [dPa · S] | 1000 | 1500 | 1000 |

As clear from the results presented in Tables 1 to 3, in the patch of the present invention, it was confirmed that the viscosity (115° C.) of the adhesive agent layer was in the range of 100 to 2500 dPa·s, and the tackiness evaluation and the residual adhesive agent layer evaluation were both good, so that both excellent tackiness and cohesive force were achieved. On the other hand, when the mass ratio of the content of terpene-based resin and the content of rosin-based resin (TP/RS) was out of the range of the present invention (Comparative Examples 1 to 4), and when the mass ratio of the content of styrene-isoprene-styrene block copolymer and the content of liquid paraffin (SIS/LP) was out of the range of the present invention (Comparative Examples 5 and 6), it was confirmed that the excellent tackiness and cohesive force as in the present invention were not achieved even when either one of the conditions was satisfied. Moreover, in the patch of the present invention, as clear from the comparison with Comparative Examples 7 and 8, it was confirmed that both of the above-mentioned excellent tackiness and cohesive force were achieved even when the thickness of the adhesive agent layer was relatively large, 320 μm.

Examples 6 and 7

Each of the patches was obtained in the same manner as in Example 1 except that the compositions of the adhesive agent layer compositions were changed to the compositions presented in Table 4 below and the thickness of the adhesive agent layer was changed to 250 μm (Example 6) or 400 μm (Example 7).

Examples 8 to 12

Each of the patches was obtained in the same manner as in Example 1 except that the compositions of the adhesive agent layer compositions were changed to the compositions presented in Table 4 below.

The patches obtained in Examples 6 to 12 were subjected to tackiness evaluation and residual adhesive agent layer evaluation tests as well as adhesive agent layer viscosity measurement. The results are presented in Table 4 below together with the compositions of the adhesive agent layer compositions of Examples. In addition, Table 4 also present the mass ratio of the content of terpene-based resin and the content of rosin-based resin (TP/RS), the mass ratio of the content of styrene-isoprene-styrene block copolymer and the content of liquid paraffin (SIS/LP), and the mass ratio of the content of polyisobutylene and the content of styrene-isoprene-styrene block copolymer (PIB/SIS) in the adhesive agent layer.

TABLE 4

|  | Ex. 6 | Ex. 7 | Ex. 8 | Ex. 9 | Ex. 10 | Ex. 11 | Ex. 12 |
|---|---|---|---|---|---|---|---|
| Adhesive Agent Layer Composition [Parts by Mass] | | | | | | | |
| Nonylic Acid Vanillylamide | 0.016 | 0.016 | 0.020 | 0.016 | 0.016 | 0.016 | 0.020 |
| Amur Cork Tree Powder | 1.70 | 1.70 | 1.70 | 1.70 | 1.70 | — | — |
| Glycol Salicylate | 2.55 | 2.55 | 2.55 | 2.55 | 2.55 | — | — |
| Methyl Salicylate | — | — | — | — | 5.00 | — | 10.00 |
| l-Menthol | 5.11 | 5.11 | 5.11 | 5.11 | 5.11 | 5.00 | — |
| Terpene-Based Resin (TP) | 8.00 | 8.00 | 8.00 | 9.20 | 6.82 | 8.00 | 7.70 |
| Rosin-Based Resin (RS) | 14.00 | 14.00 | 14.00 | 6.10 | 11.94 | 14.00 | 17.11 |
| Styrene-Isoprene-Styrene Block Copolymer (SIS) | 21.79 | 21.79 | 21.79 | 21.79 | 21.79 | 21.79 | 15.00 |
| Polyisobutylene (PIB) | 9.40 | 9.40 | 9.40 | 6.10 | 12.64 | 9.40 | 8.70 |
| Liquid Paraffin (LP) | 33.824 | 33.824 | 33.820 | 33.824 | 33.824 | 33.614 | 33.320 |
| Propylene Glycol | — | — | — | — | — | — | 5.00 |
| Additional Ingredients | 3.61 | 3.61 | 3.61 | 3.61 | 3.61 | 3.18 | 3.15 |
| Total | 100 | 100 | 100 | 100 | 100 | 100 | 100 |
| Thickness of Adhesive Agent Layer [μm] | 250 | 400 | 320 | 320 | 320 | 320 | 320 |
| TP/RS | 0.57 | 0.57 | 0.57 | 0.57 | 0.57 | 0.57 | 0.45 |
| SIS/LP | 0.64 | 0.64 | 0.64 | 0.64 | 0.64 | 0.65 | 0.45 |
| PIB/SIS | 0.43 | 0.43 | 0.43 | 0.28 | 0.58 | 0.43 | 0.58 |
| Evaluation | | | | | | | |
| Tackiness | 90 | 100 | 80 | 77 | 77 | 80 | 77 |
| Residual Adhesive Agent Layer | 90 | 80 | 97 | 100 | 90 | 97 | 70 |
| Viscosity [dPa · S] | 1200 | 1200 | 1200 | 1200 | 1800 | 1000 | 130 |

As clear from the results presented in Table 4, in the patch of the present invention, it was confirmed that, even when the thickness of the patch (such as Examples 6 and 7), the content of nonylic acid vanillylamide (such as Example 8), the content of PIB (Examples 9 and 10), and the presence or absence of Amur cork tree powder or the like (Example 11) were changed, the viscosity (115° C.) of the adhesive agent layer was in the range of 100 to 2500 dPa·s, and the tackiness evaluation and the residual adhesive agent layer evaluation were both good, so that both excellent tackiness and cohesive force were achieved. Moreover, it was confirmed that, even when the viscosity of the adhesive agent layer was lowered (such as Example 12), the tackiness evaluation and the residual adhesive agent layer evaluation were both good, so that both excellent tackiness and cohesive force were achieved.

INDUSTRIAL APPLICABILITY

As described above, it is possible to provide a non-aqueous patch the adhesive agent layer of which has excellent cohesive force and tackiness.

The invention claimed is:

1. A patch comprising a backing layer and an adhesive agent layer, wherein
the adhesive agent layer is non-aqueous,
the adhesive agent layer contains nonylic acid vanillylamide, terpene-based resin, rosin-based resin, styrene-isoprene-styrene block copolymer, liquid paraffin, polyisobutylene, and at least one anti-inflammatory analgesic agent selected from the group consisting of methyl salicylate, glycol salicylate, l-menthol, dl-camphor, peppermint oil, and thymol,
a content of nonylic acid vanillylamide in the adhesive agent layer is 0.005 to 0.1% by mass based on a total mass of the adhesive agent layer,
a mass ratio of a content of the terpene-based resin to a content of the rosin-based resin ((content of the terpene-based resin)/(content of the rosin-based resin)) in the adhesive agent layer is 0.45 to 1.3,
a mass ratio of a content of the styrene-isoprene-styrene block copolymer to a content of the liquid paraffin ((content of the styrene-isoprene-styrene block copolymer)/(content of the liquid paraffin)) in the adhesive agent layer is 0.45 to 1.2, and
a mass ratio of a content of the styrene-isoprene-styrene block copolymer and a content of the polyisobutylene ((content of the styrene-isoprene-styrene block copolymer):(content of the polyisobutylene)) in the adhesive agent layer is 1:0.28 to 1:0.58.

2. The patch according to claim 1, wherein the adhesive agent layer is substantially water-free.

3. The patch according to claim 1, wherein a content of the anti-inflammatory analgesic agent in the adhesive agent layer is 1 to 10% by mass based on the total mass of the adhesive agent layer.

4. The patch according to claim 1, wherein a thickness of the adhesive agent layer is 250 to 400 μm.

5. The patch according to claim 1, wherein a viscosity of the adhesive agent layer measured at 115° C. with a type B viscometer is 100 to 2500 dPa·s.

6. The patch according to claim 1, wherein the mass ratio of the content of the styrene-isoprene-styrene block copolymer and the content of the polyisobutylene in the adhesive agent layer is 1:0.33 to 1:0.44.

7. The patch according to claim 4, wherein the mass ratio of the content of the styrene-isoprene-styrene block copolymer and the content of the polyisobutylene in the adhesive agent layer is 1:0.33 to 1:0.44.

* * * * *